United States Patent
Ponsort et al.

(10) Patent No.: US 8,327,853 B2
(45) Date of Patent: Dec. 11, 2012

(54) BISTABLE MAGNETIC HOLDING DEVICE

(75) Inventors: Dominique Ponsort, Bievres (FR);
Alain Riwan, Chevilly-Larue (FR); Julie Bonnemason, Chatillon (FR)

(73) Assignee: Commissariat a l'Energie Atomique, Paris (FR)

( * ) Notice: Subject to any disclaimer, the term of this patent is extended or adjusted under 35 U.S.C. 154(b) by 203 days.

(21) Appl. No.: 12/994,448

(22) PCT Filed: May 25, 2009

(86) PCT No.: PCT/EP2009/056276
§ 371 (c)(1), (2), (4) Date: Nov. 23, 2010

(87) PCT Pub. No.: WO2009/144189
PCT Pub. Date: Dec. 3, 2009

(65) Prior Publication Data
US 2011/0073118 A1    Mar. 31, 2011

(30) Foreign Application Priority Data
May 27, 2008   (FR) ...................................... 08 53440

(51) Int. Cl.
A61G 15/00    (2006.01)
H01F 7/00     (2006.01)

(52) U.S. Cl. ........................................ 128/845; 335/234

(58) Field of Classification Search .................. 128/845; 335/234, 220, 229
See application file for complete search history.

(56) References Cited

U.S. PATENT DOCUMENTS
2007/0171016 A1 *  7/2007  Bonjean et al. ............... 335/234

FOREIGN PATENT DOCUMENTS
EP           1 811 536 A1    7/2007

OTHER PUBLICATIONS
International Search Report, PCT/EP2009/056276, dated Sep. 22, 2009.
French Preliminary Search Report, FR 08 53440, dated Nov. 25, 2008.

* cited by examiner

*Primary Examiner* — Michael Brown
*Assistant Examiner* — Ophelia A Hawthorne
(74) *Attorney, Agent, or Firm* — Nixon Peabody LLP

(57) ABSTRACT

A bistable magnetic holding device, which includes: a non-magnetic support casing in the form of a channel with a rectangular cross-section; a magnetic core including a base and three legs set perpendicularly to the base, the two outer legs and the base forming a "U"; a permanent magnet in the form of a bar inserted between the base and the middle leg; a coil surrounding the middle leg; a flat movable part; and a return motion and guidance means built into the inside walls of the support so as to allow return motion, toward the upper part of the support casing, of the magnetic core.

7 Claims, 6 Drawing Sheets

BISTABLE MAGNETIC HOLDING DEVICE

CROSS REFERENCE TO RELATED APPLICATIONS OR PRIORITY CLAIM

This application is a National Phase of PCT/EP2009/056276, filed May 25, 2009, entitled, 'BISTABLE MAGNETIC FASTENING DEVICE", and claims priority of French Patent Application No. 08 53440, filed May 27, 2008.

TECHNICAL FIELD

The invention relates to a bistable magnetic holding device.

PRIOR STATE OF THE ART

Among the devices known to the art, completely passive holding devices based on permanent magnets are widely used due to their simplicity of use, for example for holding closet doors closed. These devices have two major disadvantages, however, when they are designed to produce a strong attraction force:

The force needed to detach them is equal to their attractive force.

They tend to attract all small objects made of magnetic materials located within their reach, which is not acceptable for normal use in any environment.

There also exist devices known to the art based on electromagnets. An electromagnet is made up of a winding and a part made of soft ferromagnetic material called the magnetic core. The winding, when a current runs through it, creates a magnetic field channeled by the magnetic core. When the electromagnet is fed by an alternating current, the magnetic core is made up of thin sheets of soft iron assembled in layers, in order to avoid losses connected with the appearance of eddy currents within it. The shape given to the magnetic core makes it possible to either concentrate the effect of the magnetic field, or to channel it. Such an electromagnet makes it possible to produce an electromagnetic force, or to produce a controlled magnetic field in a region of space.

Devices combining a permanent magnet with a coil are also known. The permanent magnet exerts an attractive force which can be cancelled by an opposing magnetic induction when the coil is energized. The device is said to be in the closed position when the magnetic circuit is closed by a movable part attracted by the magnet, and in the open position when no force is exerted. It is also possible to make systems that are bistable, that is able to take on two stable positions in the absence of current, for example by using a spring to attract the movable armature with a force greater than the attractive force of the magnet in the open position.

The document referenced as [1] at the end of the description thus describes a magnetic device with a permanent magnet 13. As shown in FIG. 1, this device is made up of a coil 14 surrounded by a magnetic core with two legs 12.1, 12.2 outside of coil 14 and a middle leg 11 passing through the coil, as well as a movable armature 21 and a yoke 22 opposite, magnetically connecting the three legs, a permanent magnet 13 being placed at one end of the middle leg 11 on the same side as yoke 22. Middle leg 11 includes a part 15.2 which concentrates the magnetic induction of magnet 13. Air gaps g1 and g2 are located between the free ends of outside legs 12.1 and 12.2 and movable armature 21. The third air gap g3 is located between the free end of middle leg 11 and movable armature 21. Groove 16 allows this magnetic device to be attached to an external device.

In the absence of a supply of current, permanent magnet 13 attracts movable part 21, if it is close enough. Coil 14 can reinforce the induction of magnet 13 to increase the attractive force, or cancel it if it is supplied in the opposite sense. In this second case a spring can be used to detach movable armature 21 from magnet 13. To obtain a stable position, coil 14 not being supplied with current, the spring's holding force must be greater than that of the permanent magnet.

Such a magnetic device has the disadvantage of attracting magnetic parts, located within reach of the magnet, which may then come between the permanent magnet 13 and the movable part 21, preventing it from attaching itself.

The purpose of the invention is to correct the disadvantages described above by proposing a bistable magnetic holding device whose transition from the open condition to the closed condition, caused by the adhesion of the movable part, can be electrically controlled, and whose position in the open condition is set back from its surroundings, which prevents unintentionally attracting small magnetic objects found there, transition between the open condition and the closed condition being possible only in the presence of the matching movable part.

DISCLOSURE OF THE INVENTION

The invention relates to a bistable magnetic holding device, characterised in that it comprises:
- a non-magnetic support casing forming a channel with a rectangular cross-section,
- optionally a plate made of nonmagnetic material, free to move in translation within this support casing, parallel to its sides, on which rests
- a magnetic core including a base and three legs set perpendicularly to this base, the two outer legs and the base forming a 'U,'
- a permanent magnet in the form of a bar inserted between the base and the middle leg,
- a coil surrounding the middle leg,
- a flat movable magnetic part located above the upper part of the support casing, a magnetic flux aligned in the direction of motion of this flat movable part being established between the magnetic core and this movable part,
- return motion and guidance means built into the internal side walls of the support casing, and optionally the ends of the plate, so as to allow an upward return motion of the magnetic core to a position where the three ends of the upper part of the three legs are in contact with the lower surface of the top of the support casing, and to allow guidance in translation of the outside surfaces of the two outer legs of the magnetic core within the support casing.

Advantageously, the return and guidance means include two elongated L-shaped parts, each associated with a return spring.

Advantageously, the nonmagnetic support casing can be a closed casing. It can be made of plastic.

The invention also relates to an orthopaedic device including a device according to the invention, in which the arm of a user is set in a conformal shell built integral with a movable magnetic part.

BRIEF DESCRIPTION OF DRAWINGS

Other characteristics, purposes and advantages will appear in the description that follows, which is purely illustrative and not limiting, and should be read with reference to the annexed figures which illustrate embodiments of the process and device according to the invention.

DETAILED DISCLOSURE OF SPECIFIC EMBODIMENTS

Figure 1:
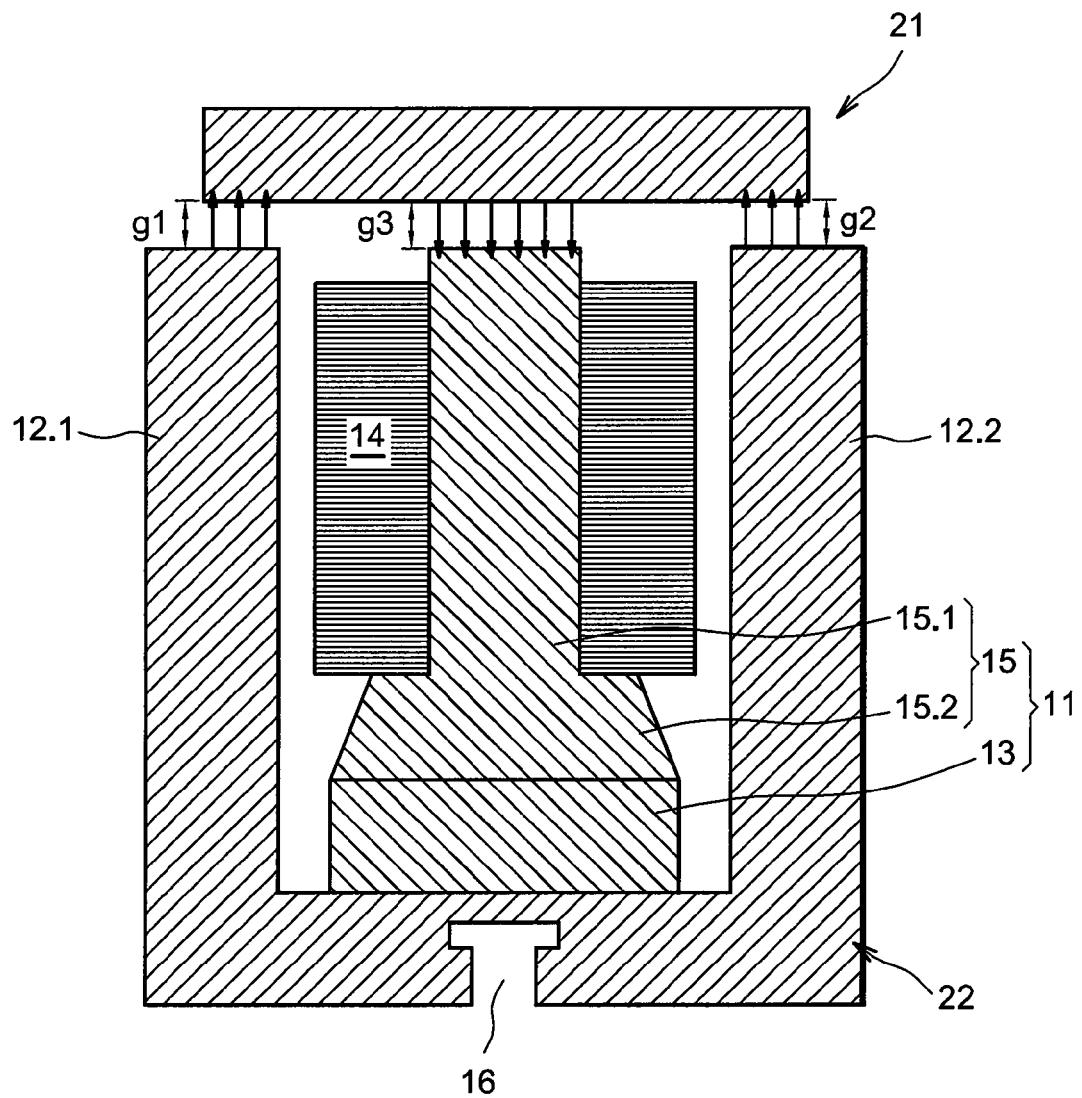
FIG. 1 shows a prior art bistable device.
Figure 2A:
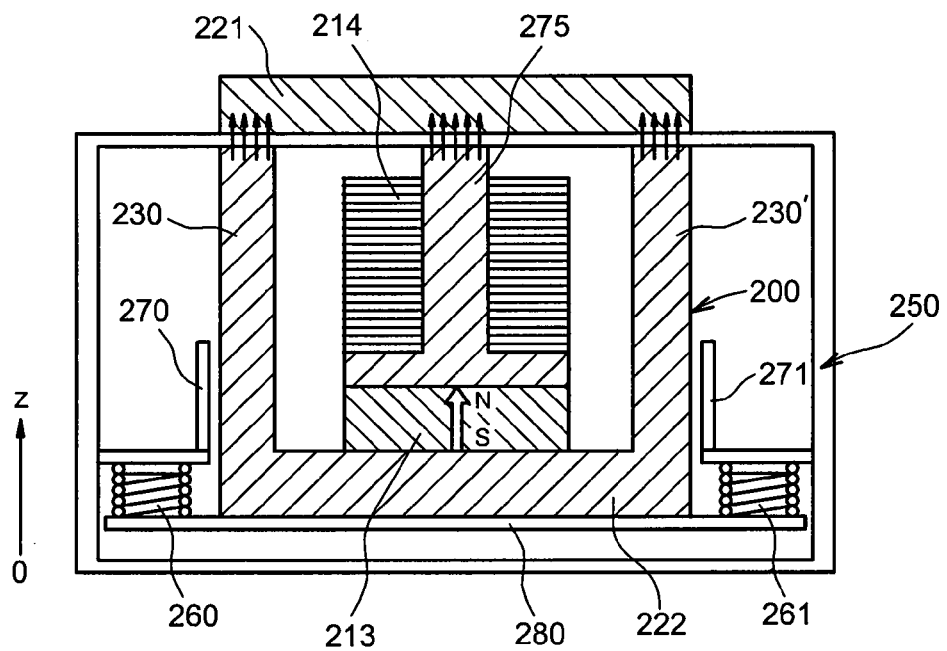
FIG. 2A shows a bistable device according to the invention in a first stable position.
Figure 2B:
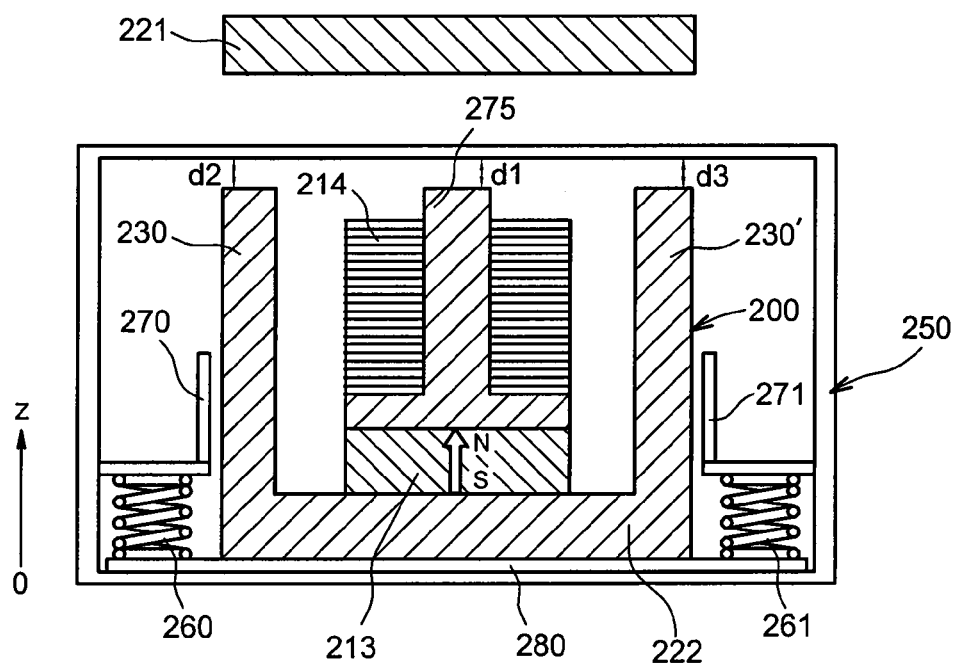
FIG. 2B shows a bistable device according to the invention in a second stable position.

FIGS. 2A and 2B show the bistable magnetic holding device of the invention in, respectively, a stable closed position and in a stable open position.

This bistable magnetic holding device includes:
- a non-magnetic support casing 250 forming a channel with a rectangular cross-section,
- optionally a plate 280 made of non-magnetic material, movable in translation within this support casing 250 parallel to its side parts ($\overrightarrow{oz}$ direction), on which rests:
- a magnetic core 200 including a base 222 and three legs, to wit two outside legs 230 and 230' and a middle leg 275, arranged perpendicularly to this base, the two outside legs 230 and 230' and base 222 forming a "U",
- a permanent magnet 213 in the shape of a bar inserted between base 222 and middle leg 275, for example in the shape of an inverted "T", an arrow showing the north pole of this permanent magnet 213,
- a coil 214 surrounding middle leg 275,
- a flat movable magnetic part 221 located above the upper part of the support casing 250, a magnetic flux aligned in the direction of motion $\overrightarrow{oz}$ of this flat movable part being established between the magnetic core and this movable part,
- return motion means 260 and 261 and guidance means 270 and 271 built into the inner side walls of support casing 250 and, optionally, into the ends of plate 280, so as to allow an upward return of magnetic core 200 to a position of contact between the upper part of the three legs 230, 275, 230' and the lower surface of the upper part of support casing 250, and to allow guidance in $\overrightarrow{oz}$ translation of the outside surfaces of the outer legs of the magnetic core within the support casing.

Advantageously, the return and guidance means include two elongated L-shaped parts 270, 271, made up for example of two rectangular parts set at right angles to one another, each associated with a return spring 260, 261.

In the stable closed position shown in FIG. 2A, movable part 221 adheres to the upper surface of the upper part of nonmagnetic support casing 250. This movable part 221 is strongly attracted by the magnetic core associated with coil 214. Springs 260 and 261 are compressed, their return force being less than the magnetic attraction thus created.

In the stable open position, shown in FIG. 2B, movable part 221 is free and no longer adheres to the upper surface of the upper part of nonmagnetic support 250. Return springs 260 and 261 then hold the magnetic core 200 at a set distance ($d_1$, $d_2$, $d_3$) from the lower surface of the upper part of the support casing 250. This distance is large enough that no metallic object present in the surroundings (including movable part 221) is attracted. It is, moreover, small enough that the magnetic core associated with the coil is able to attract movable part 221 with a force greater than the weight of magnetic core 200, coil 213 and plate 280 plus the return force of springs 260 and 261, in order to attain the closed position shown in FIG. 2A. It should be noted that the transition from the open position to the closed position is possible only in the presence of movable part 221.

FIGS. 3A to 3F show a cycle of operation of the device of the invention, showing the transition steps.

Figure 3A:
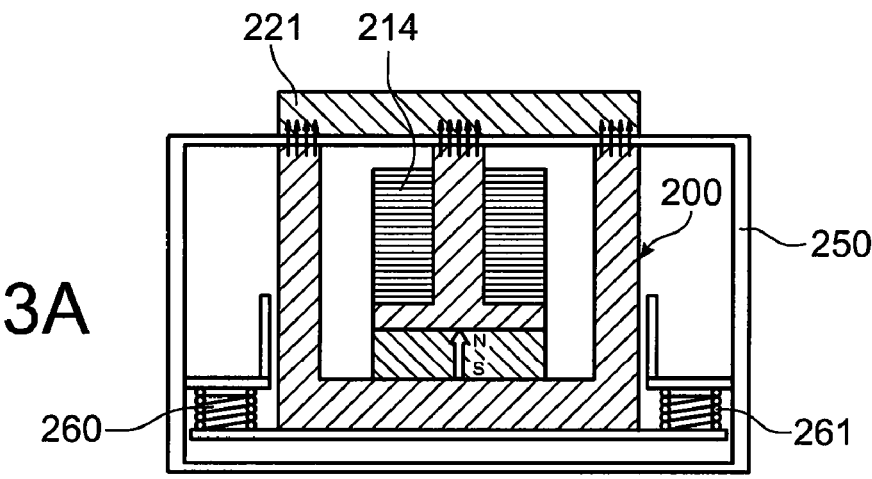
FIGS. 3A-3F show a cycle of operation according to the invention.

FIG. 3A shows a first step, in which the device is in the stable closed position. Coil 214 is not supplied with current. Movable part 221 is attracted by magnet 213. Return springs 260, 261 are compressed.

Figure 3B:
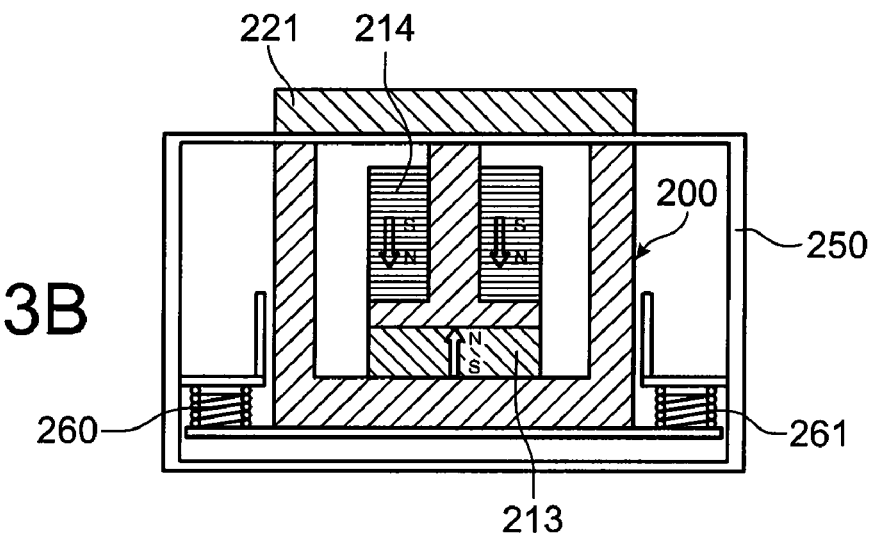

FIG. 3B shows the following step, in which coil 214 is supplied with current in such a way that its field opposes that of magnet 213 and exactly cancels the attractive force on movable part 221.

Figure 3C:
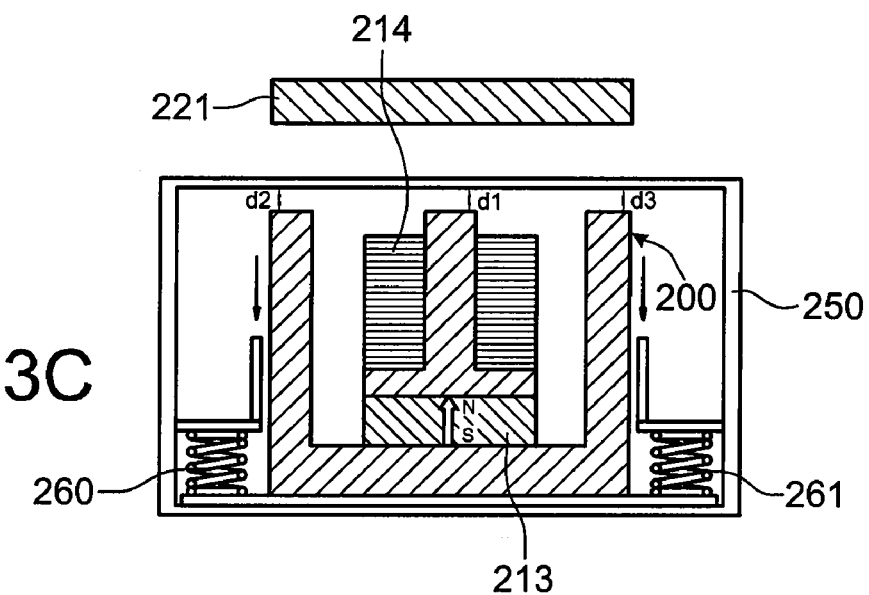

In the following step, shown in FIG. 3C, return springs 260 and 261 repel magnetic core 200 which moves away from the upper part of nonmagnetic support casing 250. As a result, movable piece 221 is released. The supply of current to coil 214 can be cut off. This is the stable open position.

Figure 3D:
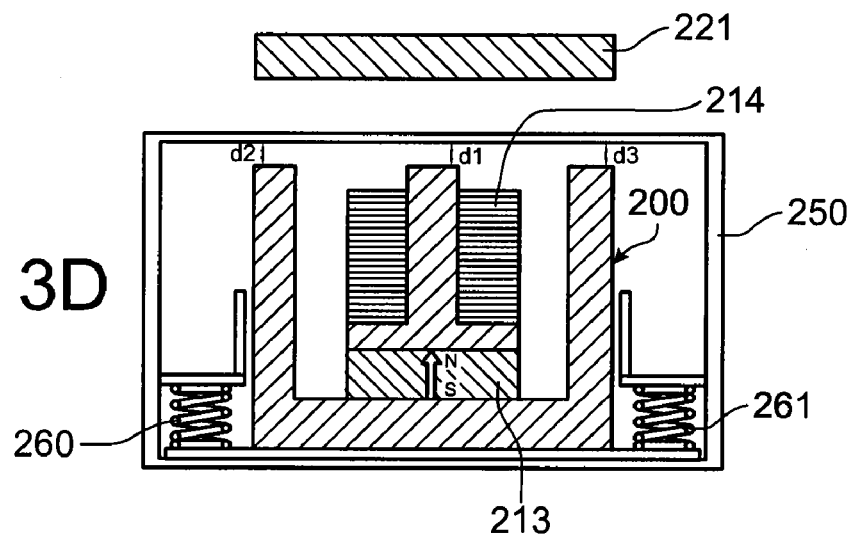

In the following step, shown in FIG. 3D, coil 214 is no longer supplied with current, and external magnetic pieces are not attracted by the magnetic core.

Figure 3E:
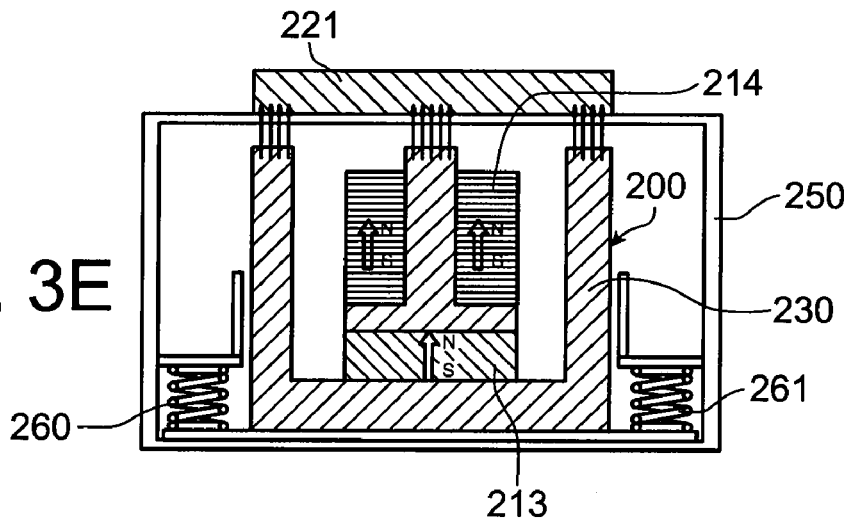

In the following step, shown in FIG. 3E, movable part 221 is brought into position on the upper surface of the upper part of non magnetic support 250. Coil 214 is supplied with current in such a way that its field is added to that of magnet 213. The force created between mobile part 221 and magnetic core 230 is sufficient to overcome that of springs 260, 261. Magnetic core 200 is pressed against the lower surface of the upper part of nonmagnetic support 250. If movable part 221, which is used to close magnetic circuit 230, is not positioned on the upper surface of nonmagnetic support 250, nothing happens.

Figure 3F:
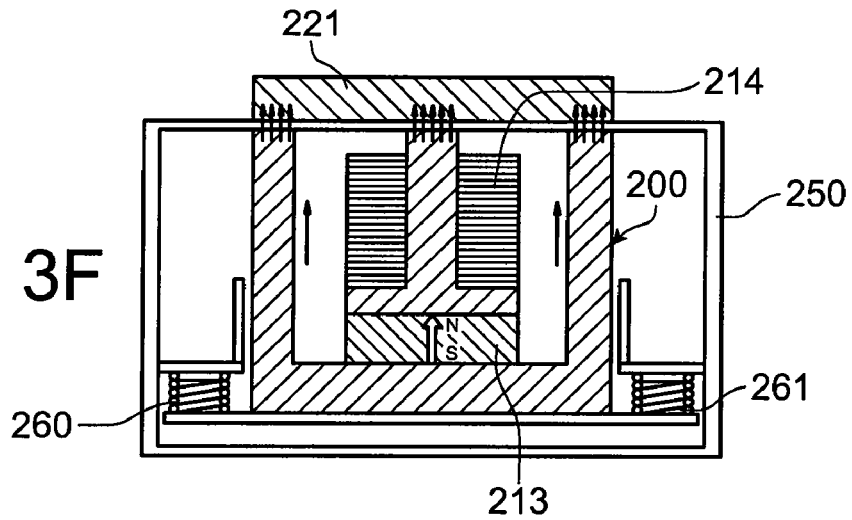

Finally, in a last step shown in FIG. 3F, the current supply to the coil is cut off and the stable closed position is restored, as shown in FIGS. 2A and 3A.

Alternative Embodiments

Figure 4A:
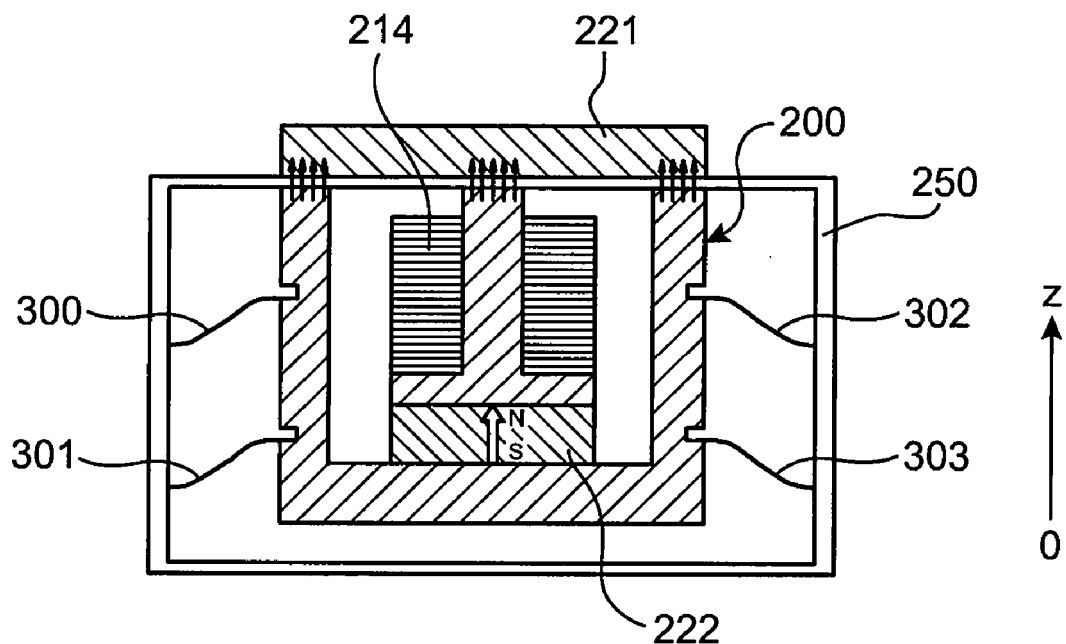
FIGS. 4A, 4B show a variant of the device according to the invention in a stable closed position and a stable open position, respectively.
Figure 4B:
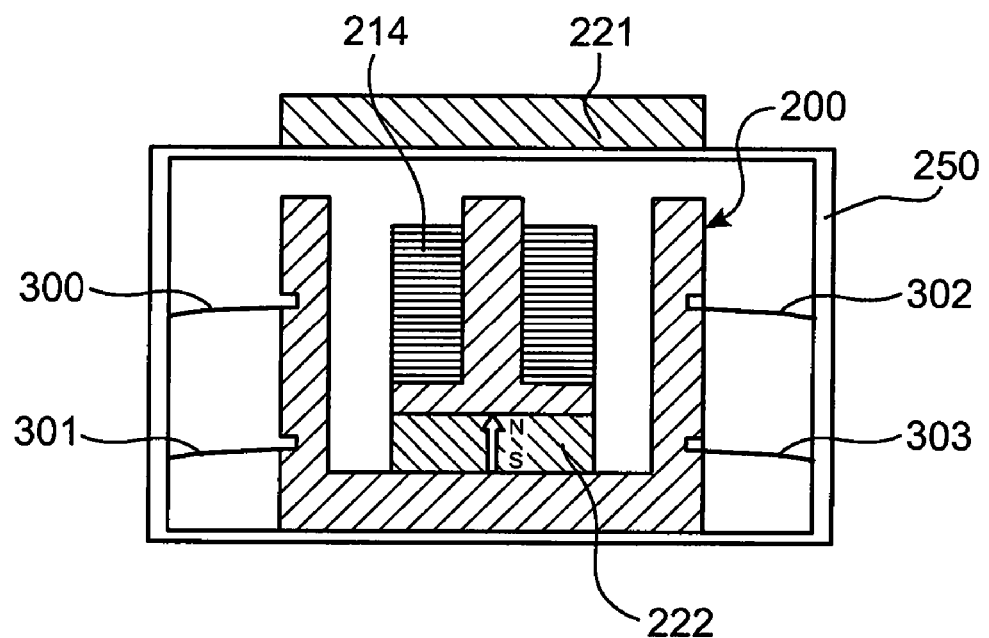

In one variant of the device according to the invention, the return spring function is combined with the translational guidance function by using leaf springs. In FIGS. 4A and 4B, leaf springs 300, 301, 302 and 303 form a deformable parallelogram which guides magnetic core 200 along axis $\overrightarrow{oz}$. The leaf springs can optionally be built into support casing 250. FIG. 4A shows the stable closed position and FIG. 4B shows the stable open position.

Figure 5:
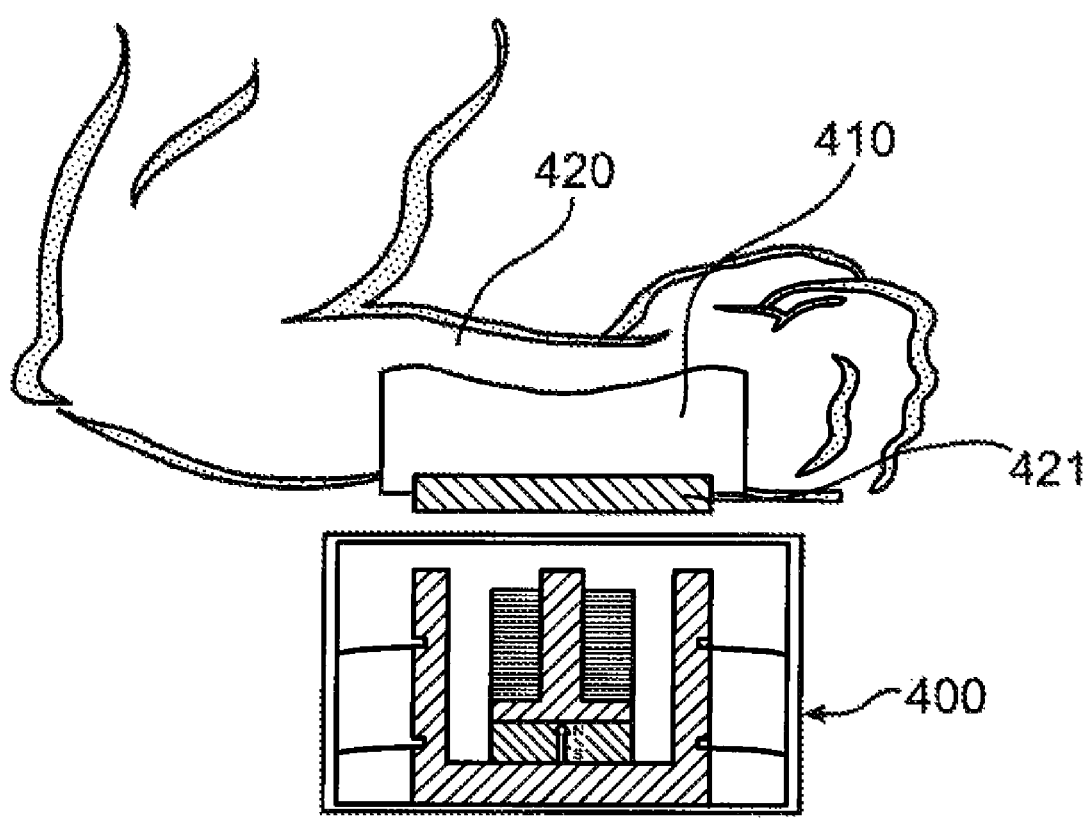
FIG. 5 shows an application of the device of the invention.

FIG. 5 shows an application in which the device 400 of the invention is used to hold an arm in an orthopaedic device. The movable magnetic part 421 is built into a conformal shell 410 which provides the interface with this arm 420. When the arm is pressed against the support casing, it is possible to initiate the attachment phase by supplying the coil with current in the correct direction. Once attachment is achieved, the supply to the coil can be cut off. The coil need only be supplied in the opposite sense to release the arm.

The invention claimed is:
1. A bistable magnetic holding device, characterised in that it comprises:
   a nonmagnetic support casing forming a channel with a rectangular cross-section, a magnetic core including a base and three legs arranged perpendicularly to this base, the two outer legs and the base forming a "U", a permanent magnet in the shape of a bar inserted between the base and the middle leg, a coil surrounding the middle leg, a movable flat magnetic part set above the upper part of the support casing, a magnetic flux, aligned with the direction of motion of this movable magnetic part, being established between the magnetic core and this movable magnetic part, return motion and guidance means built into the inside walls of the support casing so as to allow a return, toward the upper part of the support casing, of the magnetic core to a position where the upper part of the three legs is in contact with the lower surface of the upper part of the support casing, and to allow the guidance in translation of the outside surfaces of the outside legs of the magnetic core within the support casing.

2. The device according to claim 1, which includes a plate, made of nonmagnetic material, movable in translation within the support casing, parallel to its side walls on which rests the magnetic core.

3. The device according to claim 2, in which the return and guidance means are built into the ends of the plate.

4. The device according to claim 1, in which the return and guidance means include two elongated L-shaped parts, each associated with a return spring.

5. The device according to claim 1, in which the nonmagnetic support casing is an enclosed casing.

6. The device according to claim 1, in which the nonmagnetic support casing is made of plastic.

7. An orthopaedic device including a device according to claim 1, in which the arm of a user is set in a conformal shell built into a flat movable magnetic part.

* * * * *